United States Patent [19]

Couchoud

[11] 4,117,042
[45] Sep. 26, 1978

[54] AROMATIC POLYPHENYL PHOSPHONATES

[75] Inventor: Paul Couchoud, Dardilly, France

[73] Assignee: Rhone-Poulenc-Textile, Paris, France

[21] Appl. No.: 790,997

[22] Filed: Apr. 26, 1977

[30] Foreign Application Priority Data

May 5, 1976 [FR] France .................. 76 13664

[51] Int. Cl.² ........................................... C07F 9/40
[52] U.S. Cl. ........................... 260/930; 260/45.7 P; 260/973; 560/67
[58] Field of Search .................. 260/930, 973

[56] References Cited

U.S. PATENT DOCUMENTS

| 2,435,252 | 2/1948 | Toy | 260/973 X |
| 2,964,477 | 12/1960 | Pilat, et al. | 260/973 X |
| 4,044,074 | 8/1977 | Walsh | 260/930 X |

*Primary Examiner*—Anton H. Sutto
*Attorney, Agent, or Firm*—Stevens, Davis, Miller & Mosher

[57] ABSTRACT

New compounds are disclosed for obtaining novel polymeric flameproofing agents. The former are diphenols of the general formula:

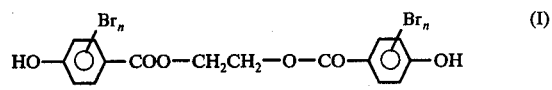

where n = 0 or 2. The latter are aromatic polyphenylphosphonates having recurring units of the general formula:

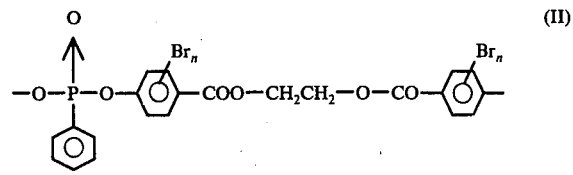

in which n equals 0 or 2, and are obtained by reacting (I) with phenylphosphonyl chloride. The latter are especially useful for the flameproofing of polyester and finished or shaped articles based on polyester.

1 Claim, No Drawings

AROMATIC POLYPHENYL PHOSPHONATES

The present invention relates to new diphenols and to a process for obtaining them, as well as to the use of such compounds for obtaining polyphenylphosphonates of dihydroxybenzoates which have an excellent flameproofing action on polyesters, and in particular on polymethylene terephthalates.

It is already known from French Application No. 2,081,803, published on the 10th Dec. 1971, to use as flameproofing agents for polyesters, polyphenylphosphonates of aromatic diols, the polyphenylphosphonates having recurring units of the formula:

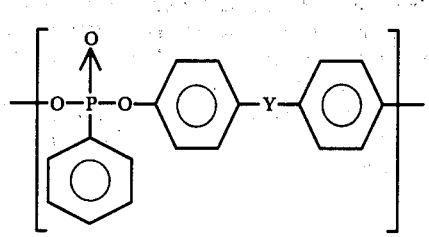

in which Y represents an alkylidene or a cycloalkylidene group having from 1 to 6 carbon atoms, or a sulphonyl group. However, those flameproofing agents, which are derived from phenols, suffer from the disadvantage of lowering the stability of the polyester to light and/or of possessing a mediocre stability to hydrolysis. Moreover, when polyesters which have been thus flameproofed are subjected to the AATCC 34/69 test, they give very fluid droplets.

Linear polyesters are also known from French Application No. 2,243,958, based on dicarboxylic acids and on diols, having from 3 to 20%, expressed as mols, relative to the acid units of the polyester, of recurring units of the formula:

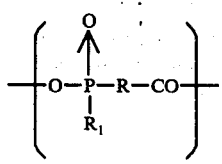

in which:
$R_1$ is a hydrocarbon radical such as a phenyl radical and R is an alkylene, arylene or aralkylene group. Flameproof yarns are obtained by spinning these polymers.

In accordance with the present invention, new phenols have now been found which can be used very advantageously for the preparation of novel flameproofing agents, the phenols having the general formula:

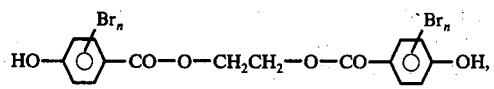

with n = 0 or 2.

The present invention also relates to a process for obtaining these new phenols by esterifying parahydroxybenzoic acid with ethylene glycol, at a temperature of between about 150° C and about 200° C, in the respective proportions of at least two mols of acid per 1 mol of ethylene glycol, and, if appropriate, subsequently brominating the product thus obtained according to any per se known process.

The present invention also relates to new aromatic polyphenylphosphonates especially useful for the flameproofing of polyesters, the recurring units of which have the general formula:

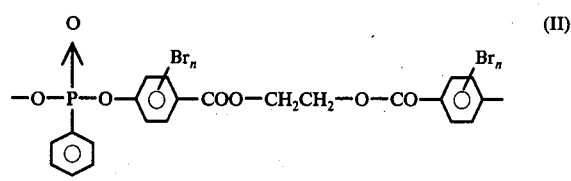

in which n equals 0 to 2.

It also relates to a process for obtaining aromatic polyphenylphosphonates of the general formula (II) by the polycondensation of the phenols of the general formula (I) with phenylphosphonyl chloride, in proportions which are substantially stiochiometric.

The phenols according to the present invention, of the general formula (I), may be prepared in various ways, for example in bulk or in solution. In the first case, the esterification of ethylene glycol with p-hydroxybenzoic acids takes place in the presence, or in the absence, of catalysts, which may be sulphuric acid, toluenesulphonic acid or phosphoric acid. The reaction takes place in the ratio of 1 mol of diol to at least 2 mols of parahydroxybenzoic acid. The temperature generally varies between 150° and 200° C; above 200° C, degradation of the parahydroxybenzoic acid occurs; the reaction time generally varies between ½ hour and 5 hours, depending on the catalyst used, and the water which is produced during the reaction is removed by distillation. Certain products, such as calcium acetate, may be added during the reaction to avoid etherification reactions.

The reaction can also take place in solution, for example in nitrobenzene, and if desired, in the presence of catalysts such as sulphuric acid or toluenesulphonic acid, the water produced again being removed by distillation.

The aromatic rings of the diphenol thus obtained may be brominated in the proportion of two atoms of bromine per ring, according to any per se known process, for example by a redox reaction (such as hydrobomic acid with hydrogen peroxide or with potassium bromate).

The new brominated or unbrominated phenols are used for the preparation of new aromatic polyphenylphosphonates intended for the flameproofing of polyesters.

The diphenols thus obtained are polycondensed with phenylphosphonyl chloride: they may be prepared by interfacial polycondensation, that is to say by dissolving each of the two components in immiscible solvents, or more simply by polycondensation in solution, in a suitable solvent such as, for example, tetrachloroethane, and preferably in the presence of a catalyst such as calcium chloride or magnesium chloride, at a temperature generally between 100° and 200° C, the starting reagents generally being present in substantially stoichiometric proportions.

The polyphenylphosphonates according to this invention may be used with polyesters such as polybutylene terephthalate and poly(1,4-dimethylene-cyclohexylene terephthalate), and they are particularly suitable for use with polyethylene terephthalate as well as with copolymers containing up to about 80% of ethylene terephthalate units, it being possible for the other units to be derived from other diacids, such as isophthalic acid, or other diols such as brominated diols of the formula:

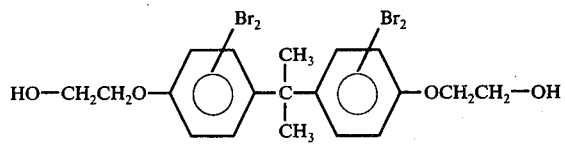

The said polyphenylphosphonates may be introduced into the bulk of the molten polyester, for example into an extruder, before extrusion in the form of yarns, films or monofilaments, in proportions which may vary between 5 and 20% by weight relative to the polymer, and preferably between about 8 and about 15%. They may also be applied at any time during the preparation of the yarns, films or monofilaments, as well as to the finished textile articles, which may be woven, knitted, and the like, by impregnating the article with the flameproofing product in the form of a solution in an appropriate solvent, for example in methylene chloride.

The thus-treated articles retain a good heat stability, a good resistance to hydrolysis, and a good stability to light.

The following examples, in which the parts and percentages are by weight, are given merely by way of illustration and without implying any limitation on the invention.

In these examples, the flameproofing tests carried out are the following:

the AATCC 34-69 test measuring the height destroyed and the number of ignited droplets;

measurement of the LOCC (Limiting Oxygen Concentration for Combustion) is effected according to the Standard Specification ASTM 2863-70 with respect to plastic test-pieces, modified and adapted for textile samples of size 5 × 16 cm, mounted on a rectangular frame;

the droplet test described in the French Journal Officiel of 26.7.1973, page 8,133, and modified by the Ministry of the Interior Decree which appeared in the French Journal Officiel of 26.2.1976, page N.C. 1,013; and the LCH inflammability meter test which is the subject of the experimental specification AFNOR G 07-113, of July 1972.

EXAMPLE 1

A. Synthesis of glycol di-p-hydroxybenzoate in bulk 0.5 mol (69 g) of p-hydroxybenzoic acid, 0.2 mol (12.4 g) of ethylene glycol, 0.69 g (1% relative to the p-hydroxybenzoic acid) of orthophosphoric acid, and 2 mg (50 ppm of Ca/glycol) of anhydrous calcium acetate, are introduced into a reactor equipped with the usual means for heating and regulating.

Heating under nitrogen is carried out until complete melting occurs; the total duration of the reaction is 2 hours, the temperature varying from 180° to 200° C, whilst the water formed is removed.

| | |
|---|---|
| Reaction yield | 67% |
| Proportion of phenolic (OH) groups | 90.5% |

The product thus obtained (a mixture of monoester and of diester) is purified by cold-washing with acetic acid.

The glycol di-p-hydroxybenzoate thus obtained has a purity of 98-99%.

B. Synthesis of glycol di-p-hydroxybenzoate in solution 5 mols (691 g) of p-hydroxybenzoic acid, 2 mols (124 g) of ethylene glycol, 3.5 g of sulphuric acid, 20 mg (50 ppm of Ca) of anhydrous calcium acetate, 800 ml of nitrobenzene and 300 ml of xylene, are introduced into a reactor equipped with the usual means for heating and regulating.

Heating under nitrogen is carried out until distillation of the xylene occurs. The reaction is carried out for 6 hours, at a reaction temperature of 132° to 175° C, with the removal of water.

After cooling, the crystalline product obtained is filtered off, washed with xylene and, after treatment with animal charcoal, recrystallized from an acetone/water mixture.

| | |
|---|---|
| Yield | 50% |
| Proportion of phenolic OH groups | 98.5% |

EXAMPLE 2

Preparation of brominated glycol di-p-hydroxybenzoate 33.40 g (0.2 mol) of potassium bromate are dissolved in 500 ml of water; 30.20 g (0.1 mol) of glycol di(p-hydroxybenzoate), prepared as in Example 1, are added and 73.64 g (0.6 mol) of 66% strength hydrobromic acid are added little by little, with a temperature increase from 20° to 40° C, over a period of 1 hour 30 minutes, the temperature being maintained at 40° C for 2 hours.

The product obtained after filtering is washed with water, then with a solution of 5% strength sodium hyposulphite, and then again with water, and is recrystallized from an acetone/water mixture.

| | |
|---|---|
| Yield | 56.80% |
| Bromine content | 49.20% |
| Proportion of phenolic OH groups | 99% |

EXAMPLE 3

Preparation of the polyphenylphosphonate of glycol dihydroxybenzoate

A reactor equipped with the usual means for heating and for regulating is charged with: 97.3 g of 98% strength glycol di-p-hydroxybenzoate, 130 cc of 1,1′,2,2′-tetrachloroethane, anhydrous calcium chloride (750 ppm of calcium relative to the diphenol), and benzene (1 ml for 1 g of diphenol).

After removing the water as the water/benzene azeotrope and distilling off the benzene, 62.7 g of 99% strength phenylphosphonyl chloride are introduced dropwise, at a temperature of 130° C, and the whole is heated for 24 hours at the reflux temperature of the 1,1′,2,2′-tetrachloroethane. A quantity of tetrachloroethane, equal to that introduced at the start, is added and the collodion is allowed to cool to ambient temperature. It is then poured dropwise, with agitation, into methanol: the polyphenylphosphonate precipitates and is subsequently filtered off, washed with methanol, dried and purified.

| | |
|---|---|
| Specific viscosity measured in a 1% strength solution at 25° C in N-methyl-pyrrolidone | 0.34 |
| Quantity of phosphorus | 7.3% |
| Purity | 97.6% |
| Stability to hydrolysis in aqueous media: | |
| pH 3 - 100° C for 3 hours: | pH variation zero |
| pH 10 - 60° C for 3 hours: | pH variation zero |

EXAMPLE 4

Preparation of the polyphenylphosphonate of brominated glycol dihydroxybenzoate

The reaction is carried out in the same way as in Example 3, using as starting compounds: 34.04 g of 99% strength brominated glycol parahydroxybenzoate, such as prepared according to Example 2, instead of glycol parahydroxybenzoate, 10.74 g of 99% strength phenylphosphonyl chloride, $CaCl_2$ (750 ppm of Ca relative to the diphenol), 46 $cm^3$ of tetrachloroethane and 30 $cm^3$ of benzene.

The product thus obtained has the following characteristics:

| | |
|---|---|
| Quantity of bromine (by weight) | 40.69% |
| Quantity of phosphorus | 4.17% |
| Purity | 99% |
| Specific viscosity (measured as in Example 3) | 0.20 |
| Melting point (measured on the DuPont 900ATD apparatus) | 125° C |
| Heat stability (DAM thermobalance Ugine Eyraud type B 60): | loss |
| 240° C isotherm under nitrogen for 2 hours | 3.1% |
| 260° C isotherm under nitrogen for 2 hours | 6.3% |

EXAMPLE 5

Three samples A, B and C are preapred from yarns made of polyethylene glycol terephthalate, having respective weights of:

| | | |
|---|---|---|
| A: | 128 g/m² | (knitted) |
| B: | 450 g/m² | (woven) |
| C: | 128 g/m² | (knitted) |

Samples A and B are treated with a solution of the polyphenylphosphonate of glycol dihydroxybenzoate, prepared according to Example 3, in methylene chloride, the samples being soaked, dried and treated on a stenter at 200° C. Sample C is treated in the same way, but with the polyphenylphosphonate of brominated glycol dihydroxybenzoate, such as prepared in Example 4. Each type of sample is treated with various percentages of flameproofing agents. The results are given in the table below.

| | % of flameproofing agent deposited | AATCC test | | Number of ignited droplets | LOCC |
|---|---|---|---|---|---|
| | | Duration, seconds | Height cm | | |
| Sample A | 0 | 200 | 26 | > 2 | 24 |
| | 8 | 100 | 26 | 0 | 31.2 |
| | 16 | 47 | 19 | 0-1 | 31.8 |
| | 20 | 110 | 21 | 0 | 33 |

| | % of flameproofing agent deposited | LCH inflammability meter | | | LOCC |
|---|---|---|---|---|---|
| | | Duration, seconds | Height cm | Surface area cm² | |
| Sample B | 13 | 49 | 12 | 33 | 31 |
| | 19 | 41 | 12 | 33 | 31 |

| | % of flameproofing agent deposited | AATCC test | | Number of ignited droplets |
|---|---|---|---|---|
| | | Duration, seconds | Height cm | |
| Sample C | 8.6 | 130 | 26 | 0 |
| | 11 | 95 | 21 | 0 |
| | 15 | 83 | 20 | 0 |

EXAMPLE 6

A knitted fabric (80 g/m²) based on a copolyester derived from polyethylene glycol terephthalate and a brominated diol of the formula:

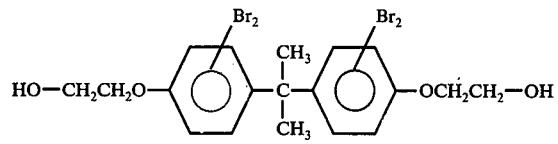

in a quantity such that the copolyester contains 5.3% of bromine, is prepared.

The knitted fabric is treated, by the method described in Example 5, with the flameproofing agent prepared according to Example 3.

| % of flameproofing agent deposited | AATCC test | | Number of ignited droplets | Droplet test |
|---|---|---|---|---|
| | Duration seconds | Height, cm | | |
| 0 | 80 | 26 | 5 | > 2 |
| 9 | 5 | 11 | 0 | 0 |
| 20 | 5 | 8 | 0 | 0 |

What is claimed is:

1. An aromatic polyphenylphosphonate consisting of recurring units of the formula:

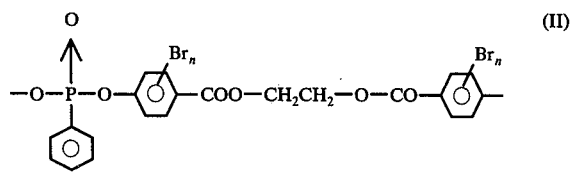

in which n equals 0 or 2.

* * * * *